(12) United States Patent
Bland et al.

(10) Patent No.: US 8,785,480 B2
(45) Date of Patent: Jul. 22, 2014

(54) FUNCTIONALIZED PYRIDINE N-OXIDES AND PROCESSES FOR THE PREPARATION OF THE SAME

(71) Applicant: Dow AgroSciences LLC, Indianapolis, IN (US)

(72) Inventors: Douglas C. Bland, Midland, MI (US); Ronald Ross, Jr., Zionsville, IN (US); Peter L. Johnson, Indianapolis, IN (US); Timothy C. Johnson, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/917,030

(22) Filed: Jun. 13, 2013

(65) Prior Publication Data

US 2014/0005403 A1    Jan. 2, 2014

Related U.S. Application Data

(60) Provisional application No. 61/666,811, filed on Jun. 30, 2012.

(51) Int. Cl.
| | |
|---|---|
| *C07D 211/92* | (2006.01) |
| *C07D 213/00* | (2006.01) |
| *C07D 213/08* | (2006.01) |
| *C07D 213/14* | (2006.01) |
| *C07D 409/00* | (2006.01) |
| *C07D 411/00* | (2006.01) |
| *A01N 43/40* | (2006.01) |
| *A01N 43/02* | (2006.01) |
| *A61K 31/44* | (2006.01) |
| *A61K 31/38* | (2006.01) |

(52) U.S. Cl.
USPC .......... 514/358; 514/336; 514/430; 546/250; 546/279.7; 546/339; 546/347

(58) Field of Classification Search
USPC ......................................... 514/358; 546/250
See application file for complete search history.

(56) References Cited

U.S. PATENT DOCUMENTS

| | | | |
|---|---|---|---|
| 4,050,921 | A | 9/1977 | Plant et al. |
| 4,212,870 | A | 7/1980 | Gibbs |
| 7,511,149 | B2 | 3/2009 | Arndt et al. |
| 7,678,920 | B2 | 3/2010 | Zhu et al. |
| 7,687,634 | B2 | 3/2010 | Loso et al. |
| 8,188,292 | B2 | 5/2012 | Loso et al. |
| 8,193,222 | B1 | 6/2012 | Bland et al. |
| 2008/0033180 | A1 | 2/2008 | Renga et al. |
| 2008/0207910 | A1 | 8/2008 | Podhorez et al. |
| 2009/0221424 | A1 | 9/2009 | Beaux et al. |
| 2010/0004457 | A1 | 1/2010 | Bland et al. |
| 2010/0168178 | A1 | 7/2010 | Qin et al. |
| 2012/0122681 | A1 | 5/2012 | Le Vezouet et al. |
| 2014/0005406 | A1* | 1/2014 | Bland et al. ........... 546/332 |

FOREIGN PATENT DOCUMENTS

| | | |
|---|---|---|
| EP | 2170066 B1 | 2/2012 |
| WO | 2010002577 | 1/2010 |
| WO | 2012084858 A2 | 6/2012 |

OTHER PUBLICATIONS

Caron, et al,: A practical, efficient, and rapid method for the oxidation of electron deficient pyridines using trifluoroacetic anhydride and hydrogen peroxide-urea complex: Tetrahedron Letters 41 (2000) 2299-2302.
Chung et al.; Synthesis of 3-Aminopyrazinone Mediated by 2-Pyridylthioimidate-ZnCl2 Complexes,Development of an Efficient Route to a Thrombin Inhibitor; J. Org. Chem 2003, 68, 8838-8846.
Degraw et al.; An Alternate Synthesis of 6-Substituted-5-deazapteridines; Bio-Organic Chemistry Laboratory, SRI International; Nov.-Dec. 1982; pp. 1461-1463.
Prikhod'ko et al; Cyclization of oximes of 3-formyl-2-acetylenylindole; pp. 2602-2604.
Albini, "Heterocyclic N-Oxides", 1991, CRC Press Chapter 2; Physical Properties; pp. 7-29.
Davies, IW, et al., "A practical, efficient, and rapid method for the oxidation of electron deficient pyridines using trifluoroacetic anhydride and hydrogen peroxide-urea complex", Tetrahedron Letters, 2000, pp. 2299-2302; abstract; pp. 2300-2301, table 3, compound 5, vol. 41, Groton, CT.
International Search Report dated Nov. 22, 2013 from application No. PCT/US2013/45333.
International Search Report dated Nov. 22, 2013 from application No. PCT/US2013/45556.
International Search Report dated Nov. 26, 2013 from application No. PCT/US2013/045300.
U.S. Appl. No. 13/919,035, filed Jun. 17, 2013.

* cited by examiner

*Primary Examiner* — John Mabry
*Assistant Examiner* — Daniel Carcanague
(74) *Attorney, Agent, or Firm* — Carol D. Corvin; Maschoff Brennan

(57) ABSTRACT

In one embodiment, processes for the preparation of certain functionalized pyridine N-oxides are provided. In one form, the functionalized pyridine N-oxides include 2-substituted-5-(1-alkylthio)alkyl-pyridine N-oxides. Further embodiments, forms, objects, features, advantages, aspects, and benefits shall become apparent from the description.

21 Claims, No Drawings

FUNCTIONALIZED PYRIDINE N-OXIDES AND PROCESSES FOR THE PREPARATION OF THE SAME

CROSS-REFERENCE TO RELATED APPLICATIONS

The present application claims priority to U.S. Provisional Patent Application No. 61/666,811 filed Jun. 30, 2012, the content of which is incorporated herein by reference in its entirety.

FIELD OF THE INVENTION

The invention disclosed in this document is related to the field of certain functionalized pyridine N-oxides including, for example, 2-substituted-5-(1-alkylthio)alkyl-pyridine N-oxides, and to techniques for preparing and using the same.

BACKGROUND OF THE INVENTION

Controlling pest populations is essential to modern agriculture, food storage, and hygiene. There are more than ten thousand species of pests that cause losses in agriculture. The world-wide agricultural losses amount to billions of U.S. dollars each year. Pests, such as termites, are also known to cause damage to all kinds of private and public structures resulting in billions of U.S. dollars in losses each year. Pests also eat and adulterate stored food, resulting in billions of U.S. dollars in losses each year, as well as deprivation of food needed for people.

Certain pests have or are developing resistance to pesticides in current use. Hundreds of pest species are resistant to one or more pesticides. Accordingly, there exists a continuous need for new pesticides and for processes of forming such pesticides.

U.S. Pat. Nos. 7,678,920 and 7,687,634 describe certain pesticidal sulfoximine compounds and U.S. Pat. No. 8,188,292 describes certain pesticidal sulfilimine compounds. Some of these sulfoximine and sulfilimine compounds contain a pyridine functional group. It has now been surprisingly discovered that forms of one or more of these compounds where the pyridine functional group has been N-oxidized exhibit pesticidal properties. Pyridine N-oxides are commonly prepared from direct oxidation with peracids, such as m-chloroperoxybenzoic acid (mCPBA). For some functionalized pyridines such as 2-substituted-5-(1-alkylthio)alkyl-pyridines however, the sulfide functionality is susceptible to oxidation, so direct oxidation with mCPBA is disfavored. Accordingly, there exists a need for processes of forming such N-oxidized compounds.

SUMMARY OF THE INVENTION

One embodiment disclosed herein concerns a process for the preparation of certain functionalized pyridine N-oxides including, for example, 2-substituted-5-(1-alkylthio)alkyl-pyridine N-oxides. In one more particular but non-limiting form, a process is provided for the preparation of a 2-substituted-5-(1-alkylthio)alkyl-pyridine N-oxide according to formula (I),

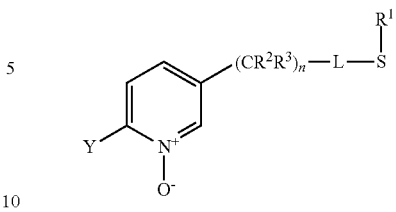

wherein

L represents a single bond or $R^1$, S and L taken together represent a 4-, 5- or 6-membered ring;

$R^1$ represents $(C_1\text{-}C_4)$ alkyl;

$R^2$ and $R^3$ individually represent hydrogen, methyl, ethyl, flouro, chloro or bromo;

n is an integer from 0-3; and

Y represents $(C_1\text{-}C_4)$ haloalkyl.

In one form, this process includes condensing an enamine according to formula (II)

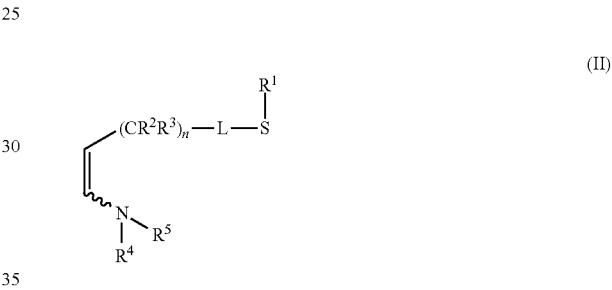

wherein $R^1$, $R^2$, $R^3$, L and n are as previously defined; and $R^4$ and $R^5$ independently represent $C_1\text{-}C_8$ alkyl, $C_2\text{-}C_8$ alkenyl, $C_1\text{-}C_8$ arylalkyl, $C_1\text{-}C_8$ haloalkyl, $C_1\text{-}C_8$ alkoxyalkyl, $C_1\text{-}C_8$ alkylaminoalkyl, aryl or heteroaryl, or $R^4$ and $R^5$ taken together with N represent a 5- or 6-membered saturated or unsaturated ring; with an α,β-unsaturated ketone according to formula (III)

wherein

Y is as previously defined; and $X^1$ represents halogen, $OR^6$, $OSO_2R^6$, $SR^6$, $SOR^6$, $SO_2R^6$ or $NR^7R^8$, where $R^6$ represents hydrogen, $C_1\text{-}C_8$ alkyl, $C_2\text{-}C_8$ alkenyl, $C_1\text{-}C_8$ arylalkyl, $C_1\text{-}C_8$ haloalkyl, $C_1\text{-}C_8$ alkoxyalkyl, $C_1\text{-}C_8$ alkylaminoalkyl, aryl or heteroaryl, and $R^7$ and $R^8$ independently represent hydrogen, $C_1\text{-}C_8$ alkyl, $C_2\text{-}C_8$ alkenyl, $C_1\text{-}C_8$ arylalkyl, $C_1\text{-}C_8$ haloalkyl, $C_1\text{-}C_8$ alkoxyalkyl, $C_1\text{-}C_8$ alkylaminoalkyl, aryl or heteroaryl or $R^7$ and $R^8$ taken together with N represent a 5- or 6-membered saturated or unsaturated ring;

to provide an intermediate compound according to formula (IV)

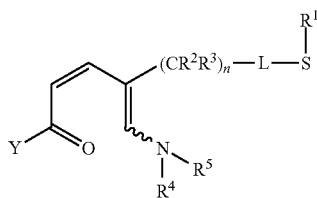

(IV)

wherein $R^1$, $R^2$, $R^3$, $R^4$, $R^5$, L and n are as previously defined. This form of the process further includes cyclizing the intermediate compound according to formula (IV) using an amine nucleophile according to formula (V)

$H_2N-X^2$ (V), wherein $X^2$ represents hydroxyl, alkoxy, cyano, amino or mercaptan, under refluxing conditions to provide a compound according to formula (I).

In another form, this process includes reacting an acetyl chloride compound according to formula (VI)

(VI)

wherein Y represents $C_1$-$C_4$ haloalkyl with an alkyl vinyl ether according to formula (VII)

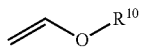

(VII)

wherein $R^{10}$ represents $C_1$-$C_4$ alkyl to provide an intermediate compound according to formula (VIII)

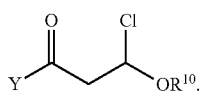

(VIII)

This form of the process further includes condensing the intermediate compound according to formula (VIII) with an enamine according to formula (II)

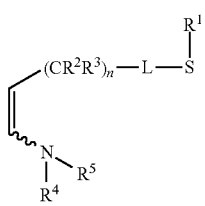

(II)

wherein $R^1$, $R^2$, $R^3$, L and n are as previously defined; and $R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl, or $R^4$ and $R^5$ taken together with N represent a 5- or 6-membered saturated or unsaturated ring to provide an intermediate compound according to formula (IV)

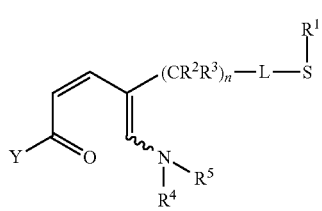

(IV)

wherein $R^1$, $R^2$, $R^3$, $R^4$, $R^5$, L and n are as previously defined.

The intermediate compound according to formula (IV) is then cyclized using an amine nucleophile according to formula (V)

$H_2N-X^2$ (V), wherein $X^2$ represents hydroxyl, alkoxy, cyano, amino or mercaptan, under refluxing conditions to provide a compound according to formula (I).

More particular but non-limiting forms of compounds of formula (I) include the following classes:

(1) Compounds of formula (I) wherein Y is $CF_3$.

(2) Compounds of formula (I) wherein $R^2$ and $R^3$ independently represent hydrogen, methyl or ethyl.

(3) Compounds of formula (I) wherein $R^1$ represents $CH_3$ and L represents a single bond, i.e., having the structure

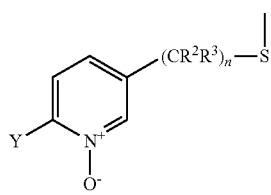

wherein n=1-3.

(4) Compounds of formula (I) wherein wherein $R^1$, S and L taken together form a saturated 5-membered ring, and n is 0, i.e., having the structure

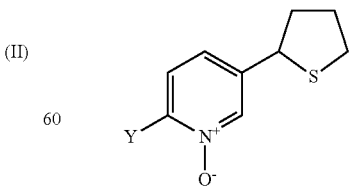

It will be appreciated by those skilled in the art that one or more combinations of the above described classes of the compound of formula (I) are possible.

In another embodiment, a novel compound according to formula (I)

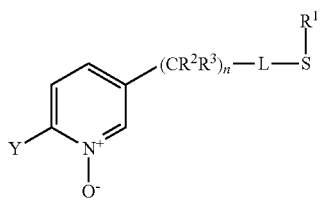

wherein

L represents a single bond or R[1], S and L taken together represent a 4-, 5- or 6-membered ring;

R[1] represents ($C_1$-$C_4$) alkyl;

R[2] and R[3] individually represent hydrogen, methyl, ethyl, flouro, chloro or bromo;

n is an integer from 0-3; and

Y represents ($C_1$-$C_4$) haloalkyl is provided.

More particular but non-limiting forms of compounds of formula (I) in this embodiment include the following classes:

(1) Compounds of formula (I) wherein Y is $CF_3$.

(2) Compounds of formula (I) wherein R[2] and R[3] independently represent hydrogen, methyl or ethyl.

(3) Compounds of formula (I) wherein R[1] represents $CH_3$ and L represents a single bond, i.e., having the structure

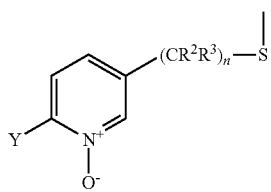

wherein n=1-3.

(4) Compounds of formula (I) wherein wherein R[1], S and L taken together form a saturated 5-membered ring, and n is 0, i.e., having the structure

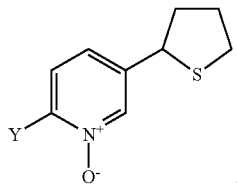

It will be appreciated by those skilled in the art that one or more combinations of the above described classes of the compound of formula (I) are possible.

Further aspects, embodiments, forms, features, benefits, objects, and advantages shall become apparent from the detailed description provided herewith.

DETAILED DESCRIPTION OF THE INVENTION

For purposes of promoting an understanding of the principles of the invention, reference will now be made to the following embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Unless specifically limited otherwise, the below listed terms as used herein shall mean the following:

"alkenyl", as used herein, means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl;

"alkoxy", as used herein, means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy;

"alkyl", as used herein, means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl;

"aryl", as used herein, means a cyclic, aromatic substituent consisting of hydrogen and carbon, for example, phenyl, naphthyl, and biphenylyl;

"halo", as used herein, means fluoro, chloro, bromo, and iodo;

"haloalkyl", as used herein, means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl; and "heteroaryl", as used herein, refers to a 5- or 6-membered aromatic ring containing one or more heteroatoms, viz., N, O or S; these heteroaromatic rings may be fused to other aromatic systems.

The compounds disclosed herein can exist as one or more stereoisomers. The various stereoisomers include geometric isomers, diastereomers and enantiomers. Thus, the compounds disclosed in this document may include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

In one embodiment, a process for the preparation of a 2-substituted-5-(1-alkylthio)alkyl-pyridine N-oxide according to formula (I)

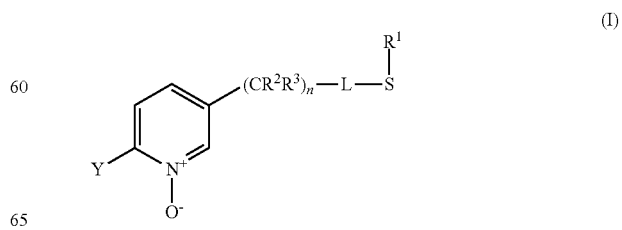

wherein

L represents a single bond or $R^1$, S and L taken together represent a 4-, 5- or 6-membered ring;

$R^1$ represents $(C_1-C_4)$ alkyl;

$R^2$ and $R^3$ individually represent hydrogen, methyl, ethyl, flouro, chloro or bromo;

n is an integer from 0-3; and

Y represents $(C_1-C_4)$ haloalkyl is provided.

In one form, this process utilizes the approach illustrated in Scheme A:

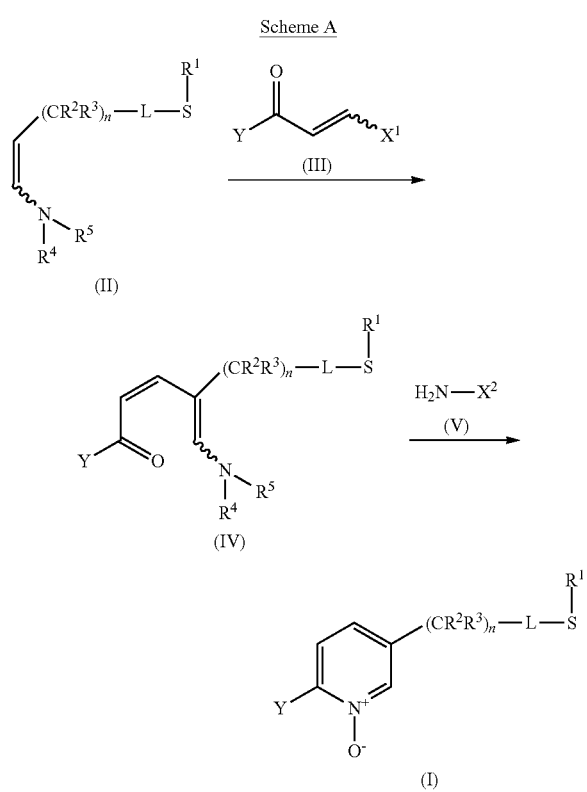

In Scheme A, an enamine according to formula (II)

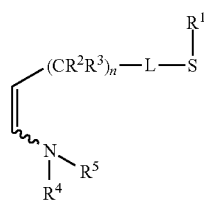

wherein $R^1$, $R^2$, $R^3$, L, and n are as previously defined; and $R^4$ and $R^5$ independently represent $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl, or heteroaryl or $R^4$ and $R^5$ taken together with N represent a 5- or 6-membered saturated or unsaturated ring;

is condensed with an α,β-unsaturated ketone according to formula (III)

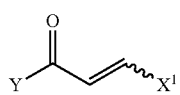

wherein

Y is as previously defined; and $X^1$ represents halogen, $OR^6$, $OSO_2R^6$, $SR^6$, $SOR^6$, $SO_2R^6$ or $NR^7R^8$, where $R^6$ represents hydrogen, $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl or heteroaryl, and $R^7$ and $R^8$ independently represent hydrogen, $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl or heteroaryl, or $R^7$ and $R^8$ taken together with N represent a 5- or 6-membered saturated or unsaturated ring;

to provide an intermediate compound according to formula (IV)

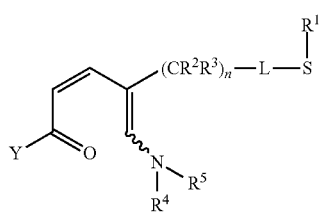

wherein $R^1$, $R^2$, $R^3$, $R^4$, $R^5$, L and n are as previously defined.

As also illustrated in scheme A, the intermediate compound according to formula (IV) is cyclized using an amine nucleophile according to formula (V)

$$H_2N-X^2 \quad (V),$$

wherein $X^2$ represents hydroxyl, alkoxy, cyano, amino or mercaptan, under refluxing conditions to provide a compound according to formula (I).

Enamines according to formula (II) can be conveniently prepared from the addition of a suitably substituted amine to an appropriately substituted aldehyde in the presence of a water adsorbing material, with or without a suitable solvent. Typically, the appropriately substituted aldehyde is reacted with an anhydrous di-substituted amine at about −20° C. to about 20° C. in the presence of a desiccant such as anhydrous potassium carbonate, and the product is isolated by routine procedures and usually used without further purification. In one non-limiting form for example where the enamine according to formula (II) has the following structure

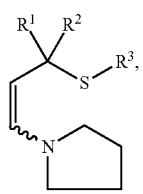

the appropriately substituted aldehyde is reacted with pyrrolidine at about −20° C. to about 20° C. in the presence of a desiccant such as anhydrous potassium carbonate, and the resulting product is isolated by routine procedures and usually used without further purification. Further details regarding the production of enamines according to formula (II) are found, for example, in U.S. Patent Publication No. 2008/0033180, the contents of which are hereby incorporated herein by reference in their entirety.

α,β-unsaturated ketones according to formula (III) are commercially available or can be prepared from the corresponding vinylogous substrates and acylating agents. In one form for example, alkylvinyl ethers can be acylated with haloalkylacetic anhydrides to yield compounds according to formula (III).

Approximately equimolar quantities of the enamine according to formula (II) and the α,β-unsaturated ketone according to formula (III) are required in the condensation process.

In one form, the condensation is conducted at a temperature from about −20° C. to about 35° C. In another more particular form, temperatures from about −5° C. to about 20° C. are used.

The condensation of the enamine according to formula (II) with the α,β-unsaturated ketone according to formula (III) may be conducted in a polar or non-polar solvent, although forms in which it is conducted in solvent-free conditions are also contemplated. Non-limiting examples of polar solvents include dichloromethane, tetrahydrofuran, ethyl acetate, acetone, dimethylformamide, acetonitrile, and dimethyl sulfoxide, while non-limiting examples of non-polar solvents include hydrocarbon and aromatic hydrocarbon solvents such as toluene. In one particular but non-limiting form, this condensation is conducted in toluene.

In one aspect, the α,β-unsaturated ketone according to formula (III) is added to a preformed mixture of the enamine according to formula (II).

In a typical condensation reaction, the enamine according to formula (II) is dissolved in the desired solvent at about −5° C. to about 20° C. and the α,β-unsaturated ketone according to formula (III) is continuously added via addition funnel to this solution. The mixture is agitated until the enamine according to formula (II) and the α,β-unsaturated ketone according to formula (III) are consumed. With the use of a non-polar solvent such as toluene, the intermediate compound according to formula (IV) can be used as is without further isolation or purification.

The cyclization of the intermediate compound according to formula (IV) with an amine nucleophile according to formula (V) is performed under refluxing conditions; i.e., at a temperature in the range of 50° C. to 90° C. As indicated above, $X^2$ may represent hydroxyl, alkoxy, cyano, amino or mercaptan. It is also possible for the amine nucleophile used in reaction Scheme A to be present in the form of an acid salt. When an acid salt form of the amine nucleophile is used, a non-nucleophilic base is also used to neutralize the acid salt analog. Non-limiting examples of non-nucleophilic bases include carbonate salts, triethylamine, N,N-diisopropylethylamine, and 1,8-diazabicycloundec-7-ene. In one non-limiting form where $X^2$ represents hydroxyl and the compound according to formula (V) is hydroxylamine, hydroxylamine hydrochloride is used in reaction Scheme A along with triethylamine Still, it should be appreciated that other variations in the amine nucleophile according to formula (V) and the non-nucleophilic base, when present, are possible and contemplated.

The cyclization of the intermediate compound according to formula (IV) may be conducted in the same solvent as the condensation of the enamine according to formula (II) and the α,β-unsaturated ketone according to formula (III).

In another form, the process of this embodiment utilizes the approach illustrated in Scheme B:

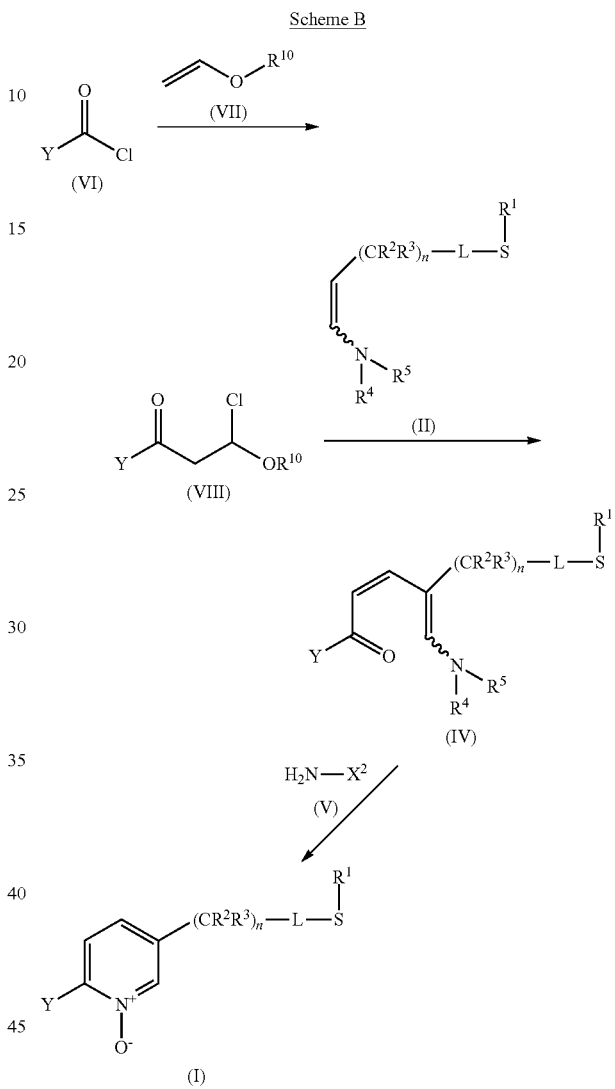

In Scheme B, an acetyl chloride compound according to formula (VI) where Y represents $C_1$-$C_4$ haloalkyl is reacted with an alkyl vinyl ether according to formula (VII) where $R^{10}$ represents $C_1$-$C_4$ alkyl. Approximately equimolar quantities of compounds according to formulas (VI) and (VII) are generally used in the process, although excesses of one or the other may be employed. In one particular form, a 10-50 percent stoichiometric excess of the alkyl vinyl ether according to formula (VII) is utilized.

This reaction is conducted either in the absence of a solvent, e.g., with excess of the alkyl vinyl ether according to formula (VII), or in the presence of an anhydrous organic solvent. Non-limiting examples of suitable solvents are hydrocarbon solvents, including aromatic hydrocarbons such as toluene. The reaction may be conducted at a temperature from about −10° C. to about 35° C. In one particular form, temperatures from about 0° C. to about 20° C. are used. In a typical reaction, the acetyl chloride compound according to formula (VI) is bubbled below the surface of the alkyl vinyl ether compound according to formula (VII), either neat or in the presence of a hydrocarbon solvent, between 0-5° C. The reaction is allowed to warm with stirring for about 1 hour, keeping the temperature no higher than room temperature. The crude reaction mixture containing the intermediate compound according to formula (VIII) may be used as is without further isolation or purification of the reaction mixture.

The intermediate compound according to formula (VIII) is then condensed with an enamine according to formula (II) in the presence of a tertiary amine base to provide an intermediate compound according to formula (IV) where Y represents $C_1$-$C_4$ haloalkyl. Approximately equimolar quantities of the intermediate compound according to formula (VIII) and the enamine according to formula (II) are required in the condensation process; at least one equivalent of tertiary amine base is required with between about 1 and about 2 equivalents being utilized in certain forms.

This condensation may be conducted at a temperature from about −20° C. to about 35° C. In one particular form, temperatures from about −5° C. to about 20° C. are utilized. This condensation may be conducted in a non-polar or polar aprotic solvent. Exemplary non-polar solvents include hydrocarbon solvents and aromatic hydrocarbons. Polar aprotic solvents are also a good choice for this chemistry. Either acetonitrile or toluene is used in particular but non-limiting forms. In one form, the intermediate compound according to formula (VIII) is added to a preformed mixture of the enamine according to formula (II) and a tertiary amine base. In a typical condensation reaction, the enamine according to formula (II) and at least a stoichiometric amount of a tertiary amine base are dissolved in the desired solvent at about −50° C. to about 200° C. and the intermediate compound according to formula (VIII) is continuously added via addition funnel to this solution. The mixture is agitated until the intermediate compound according to formula (VIII) and the enamine according to formula (II) are consumed. The intermediate compound according to formula (IV) may be used as is without further isolation or purification. Further details regarding the foregoing steps of the approach of Scheme B are provided in International Patent Publication No. WO 2010/002577, the contents of which are hereby incorporated herein by reference in their entirety.

As further illustrated in Scheme B, the intermediate compound according to formula (IV) prepared by this approach is then cyclized using an amine nucleophile according to formula (V) as discussed above.

More particular but non-limiting forms of compounds of formula (I) include the following classes:

(1) Compounds of formula (I) wherein Y is $CF_3$.

(2) Compounds of formula (I) wherein $R^2$ and $R^3$ independently represent hydrogen, methyl or ethyl.

(3) Compounds of formula (I) wherein $R^1$ represents $CH_3$ and L represents a single bond, i.e., having the structure

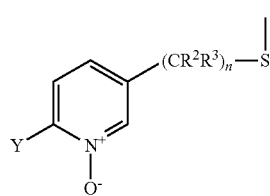

wherein n=1-3.

(4) Compounds of formula (I) wherein wherein $R^1$, S and L taken together form a saturated 5-membered ring, and n is 0, i.e., having the structure

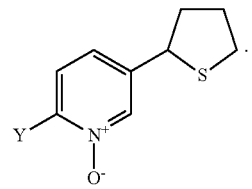

It will be appreciated by those skilled in the art that one or more combinations of the above described classes of the compound of formula (I) are possible.

The 2-substituted-5-(1-alkylthio)alkyl-pyridine N-oxides described herein may be used, for example, in place of corresponding 2-substituted-5-(1-alkylthio)alkyl-pyridine intermediates in the preparation of various N-substituted sulfilimine and sulfoximine pyridine compounds described in, for example, U.S. Pat. Nos. 7,678,920, 7,687,634 and 8,188,292, in order to prepare N-substituted sulfilimine or sulfoximine pyridine N-oxide compounds. The contents of U.S. Pat. Nos. 7,678,920, 7,687,634 and 8,188,292 are hereby incorporated herein by reference in their entirety.

Accordingly, in a further embodiment, a method for the preparation of certain N-substituted sulfilimine or sulfoximine pyridine N-oxide compounds according to formula (IX)

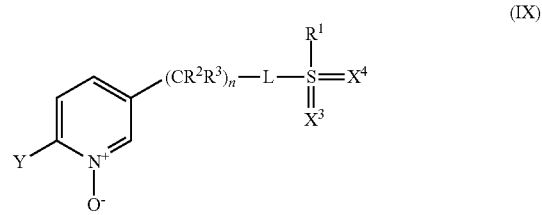

wherein,
wherein $R^1$, $R^2$, $R^3$, L, n and Y are as previously defined;
$X^3$ is optional and represents O when present;
$X^4$ represents $NNO_2$, NCN, $NCOOR^9$ or $NCONH_2$; and
$R^9$ represents ($C_1$-$C_3$) alkyl;

using the 2-substituted-5-(1-alkylthio)alkyl-pyridine N-oxides disclosed herein is illustrated in reaction Scheme C:

Scheme C

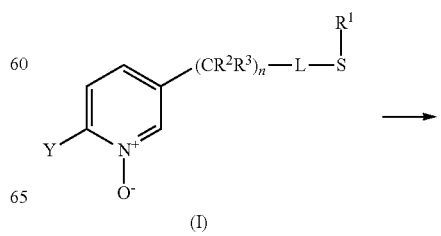

(I)

-continued

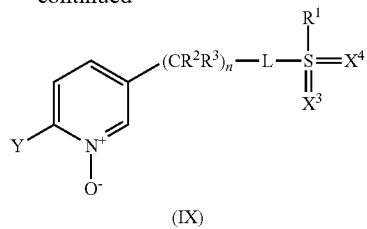

(IX)

Depending on the desired final form of the compound according to formula (IX), Scheme C is representative of the addition of $X^4$ to a compound according to formula (I) to provide an N-substituted sulfilimine pyridine N-oxide compound, or the addition of both of $X^3$ and $X^4$ to a compound according to formula (I) to provide an N-substituted sulfoximine pyridine N-oxide compound.

In one form, preparation of an N-substituted sulfilimine pyridine N-oxide compound where $X^4$ represents $NNO_2$ involves the reaction of a compound according to formula (I) with nitramide in the presence of acetic anhydride in Scheme C. In another form, preparation of an N-substituted sulfilimine pyridine N-oxide compound where $X^4$ represents NCN involves the oxidation of a compound according to formula (I) with iodobenzene diacetate in the presence of cyanamide in Scheme C. This oxidation can be carried out in a polar aprotic solvent such as $CH_2Cl_2$. Further details regarding preparations of N-substituted sulfilimine pyridines of this nature and in which the 2-substituted-5-(1-alkylthio)alkyl-pyridine N-oxides disclosed herein could be used to provide corresponding N-substituted sulfilimine pyridine N-oxides are disclosed in U.S. Pat. No. 8,188,292.

Preparation of N-substituted sulfoximine pyridine N-oxide compounds according to formula (IX), i.e., where $X^3$ is present and represents O, may be accomplished by further oxidation of the N-substituted sulfilimine pyridine N-oxide compounds described above. For example, in one non-limiting form an N-substituted sulfilimine pyridine N-oxide compound, which includes NCN added by oxidation of a compound according to formula (I) with iodobenzene diacetate in the presence of cyanamide, may be further oxidized with meta-chloroperoxybenzoic acid (mCPBA) in the presence of a base such as potassium carbonate to provide a corresponding N-substituted sulfoximine pyridine N-oxide compound. This reaction may be carried out in protic polar solvents such as ethanol and water.

Preparation of N-substituted sulfoximine pyridine N-oxide compounds according to formula (IX), i.e., where $X^3$ is present and represents O, may also be accomplished by the stepwise addition of $X^3$ and $X^4$ to a compound according to formula (I). For example, a compound according to formula (I) may be oxidized with mCPBA in a polar solvent such as dichloromethane below 0° C. to provide a sulfoxide. The sulfoxide is subsequently iminated with sodium azide in the presence of concentrated sulfuric acid in an aprotic solvent such as chloroform under heating to provide a sulfoximine.

For instances where $X^3$ is present and $X^4$ represents $NNO_2$, NCN, $NCOOR^4$, this sulfoximine can be either nitrated with nitric acid in the presence of acetic anhydride under mildly elevated temperature, or cyanated with cyanogen bromide in the presence of a base, or carboxylated with alkyl ($R^9$) chloroformate in the presence of base such as 4-dimethylaminopyridine (DMAP) to provide an N-substituted sulfoximine. Base is required for efficient cyanation and carboxylation and the preferred base is DMAP, whereas sulfuric acid is used as catalyst for efficient nitration reaction. Further details regarding preparations of N-substituted sulfoximine pyridines of this nature and in which the 2-substituted-5-(1-alkylthio) alkyl-pyridine N-oxides disclosed herein could be used to provide corresponding N-substituted sulfoximine pyridine N-oxides are disclosed in U.S. Pat. Nos. 7,678,920 and 7,687,634.

Preparation of N-substituted sulfoximine pyridine N-oxide compounds according to formula (IX) where $X^4$ represents $NCONH_2$ can be carried out by acid hydrolyzing a sulfoximine compound according to formula (IX) where NCN has been added, i.e., having the following structure

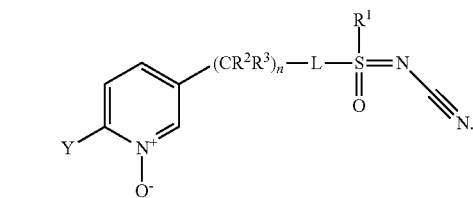

Non-limiting examples of acids that may be used in this reaction include sulfuric acid, hydrochloric acid, phosphoric acid, trifluoroacetic acid, and nitric acid.

In one form, the acid hydrolysis reaction is conducted at a temperature from about 50° C. to about 90° C. and at ambient pressure, but the use of higher or lower temperatures and pressures, if desired, is contemplated.

Non-limiting examples of solvents which can be used in the acid hydrolysis reaction include polar solvents such as dichloromethane, tetrahydrofuran, ethyl acetate, acetone, dimethylformamide, acetonitrile, and dimethyl sulfoxide.

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Molecules are given their known names, named according to naming programs within ISIS Draw, ChemDraw or ACD Name Pro. If such programs are unable to name a molecule, the molecule is named using conventional naming rules. $^1H$ and $^{13}C$ NMR spectra were performed using a Bruker 300 MHz instrument. Gas Chromatography was performed using an Agilent 6850 Network GC system or on an Agilent 6890 with the ability for cold on column injections with a capillary column. HPLC was performed using an Agi-

Example 1

Small Scale Preparation of 5-(1-(methylthio)ethyl)-2-(trifluoromethyl)pyridine N-oxide (1)

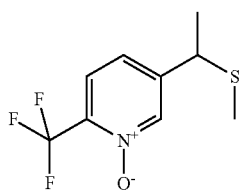

(1)

A condensation reaction of 1-(3-methylthiobut-1-enyl)pyrrolidone (2)

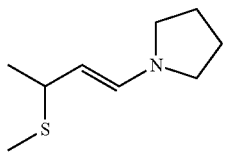

(2)

with 4-ethoxy-1,1,1-trifluorobut-3-en-2-one (3)

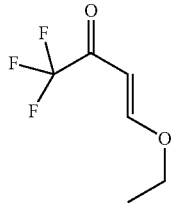

(3)

in toluene yielded a 27 wt % 1,1,1-trifluoro-6-(methylthio)-5-(pyrrolidine-1-ylmethylene)hept-3-en-2-one (4) in toluene

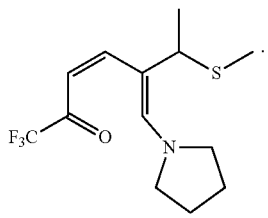

(4)

403 mg (0.37 mmol) of the 27 wt % 1,1,1-trifluoro-6-(methylthio)-5-(pyrrolidine-1-ylmethylene)hept-3-en-2-one (4) in toluene was added to a 25 mL three-neck round bottom flask equipped with a reflux condenser and vented to a bleach scrubber. To this mixture was added 34 mg (0.34 mmol) of triethylamine in one portion. The reaction mixture was cooled to about 12.8° C. and then 24 mg (0.34 mmol) of hydroxylamine hydrochloride was added in one portion. The reaction mixture was slowly heated to 85° C. and stirred for one hour and forty-five minutes. The reaction mixture was then cooled to ambient temperature. This mixture was split into many fractions for instrumental analysis and purification. A portion of the reaction mixture was partitioned between toluene and water. Both the organic and aqueous layers were analyzed by LC/MS. Both layers were confirmed to have a peak with molecular consistency for 5-(1-(methylthio)ethyl)-2-(trifluoromethyl)pyridine N-oxide ($C_9H_{10}F_3NOS$). Calculated m/z=237.04. Found m/z=237.04.

A small portion of the reaction mixture was purified using preparatory thin layer chromatography by loading 2 mL of the reaction mixture onto a 20 cm by 20 cm plate (1000 microns) and eluting it with a mixture having a ratio of 4:1 between hexanes and 2-propanol (Rf was about 0.5 to 0.6). The appropriate band was cut from the plate and extracted off of the silica gel with 20 mL of ethyl acetate. A proton NMR was taken of the best fractions of this separation. The material contained a small portion of ethyl acetate, but the chemical shifts for the desired compound are: $^1$H NMR (300 MHz, $CDCl_3$) δ 8.30 (s, 1H), 7.64 (d, J=8.3 Hz, 1H), 7.35 (d, J=8.3 Hz, 1H), 3.78 (q, J=7.1 Hz, 1H), 1.98 (s, 3H), 1.58 (d, J=7.1 Hz, 3H).

Example 2

Larger Scale Preparation of 5-(1-(methylthio)ethyl)-2-(trifluoromethyl)pyridine N-oxide (1)

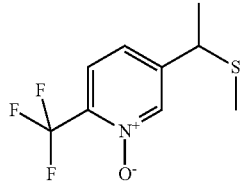

(1)

5.0 g (0.03 moles) of 1-(3-methylthiobut-1-enyl)pyrrolidone (2) and 100 mL of acetonitrile (ACN) were added to a dry 250 mL round-bottom flask equipped with a magnetic stirrer, nitrogen inlet, addition funnel, and reflux condenser. 4-ethoxy-1,1,1-trifluorobut-3-en-2-one (3) (ETFBO) (4.9 g, 0.03 mmoles) was then added dropwise over 2-3 minutes, and a resulting dark solution was stirred at room temperature for 1 hour. 2.1 g (0.03 moles) of hydroxyl amine hydrochloride was then added to this solution followed by 4.2 mL (0.03 moles) of triethylamine. The reaction was then refluxed at 85° C. for 2 hours, cooled, and an aliquot was analyzed by TLC and GC/MS which showed that the reaction was essentially complete, no starting material remained, and the existence of two new products. The major product identified upon analysis by GC/MS was consistent with the structure assigned to 5-(1-(methylthio)ethyl)-2-(trifluoromethyl)pyridine N-oxide (1), and the minor product appeared to be the trans-amination product of ETFBO and pyrrolidine. The reaction mixture was then stirred at room temperature for 12 hours, poured into about 100 mL of water and extracted with three 100 mL volumes of ethyl ether. The ether extract was washed with water and saturated aqueous sodium chloride solution, dried over anhydrous magnesium sulfate, filtered and concentrated under vacuum on a rotary evaporator. The crude product (6.1 g) was chromatographed on silica gel with a gradient of 100% hexane to 100% ethyl acetate over 20 minutes. Isolated 2.2 g of a yellow liquid which was consistent with the structure assigned to 5-(1-(methylthio)ethyl)-2-(trifluoromethyl)pyridine N-oxide (1) upon analysis by 300 MHz $^1$H NMR and GC/MS; 31% isolated yield. $^1$H NMR (300 MHz, Chloroform-d) δ 8.28 (s, 1H), 7.63 (d, J=8.3 Hz, 1H), 7.34 (d, J=8.3 Hz, 1H), 3.77 (q, J=7.1 Hz, 1H), 1.98 (s, 3H), 1.56 (d, J=7.3, 3H). Calculated m/z=237.04. Found m/z=237.04.

Example 3

Preparation of N-Cyano-S-[1-(6-trifluoromethyl-3-pyridinyethyl]-S-methylsulfilimine N-oxide (5)

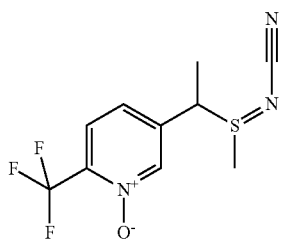

(5)

2.2 g (0.0092 moles) of 5-(1-(methylthio)ethyl)-2-(trifluoromethyl)pyridine N-oxide (1), 0.38 g (0.0092 moles) cyanamide and 100 mL of anhydrous tetrahydrofuran (THF) were added to a dry 250 mL round-bottom flask equipped with a magnetic stirrer, nitrogen inlet, and thermometer. The solution was cooled to about 4° C., and iodobenzene diacetate (3.0 g, 0.0092 moles) was added in one portion. The reaction was stirred at 0-4° C. for 2 hours, allowed to warm gradually to room temp, and then stirred at ambient temperature under nitrogen. After 13 hours, an aliquot of the reaction mixture was analyzed by HPLC using a YMC AQ column (Kyoto, Japan) with a 1.0 mL/min flow rate. Acetontitrile (ACN) and water with 0.05% trifluoroacetic acid (TFA) were used as solvents. A linear gradient was used starting at 20% ACN/80% water with 0.05% TFA and transitioning to 95% ACN/5% water with 0.05% TFA over 25 minutes. The HPLC analysis indicated that the reaction was essentially complete. The reaction mixture was then diluted with about 200 mL of ACN and washed with two 100 mL volumes of hexanes to remove the iodobenzene byproduct. The ACN solution was concentrated under vacuum on a rotary evaporator, and the resulting crude product was chromatographed on silica gel with a gradient of 50% hexanes/50% acetone that was transitioned to 100% acetone over 20 minutes. The pure fractions were combined, and concentrated under vacuum on a rotary evaporator to afford 1.7 g of a yellow solid which was consistent with the structure assigned to N-Cyano-S-[1-(6-trifluoromethyl-3-pyridinyl)ethyl]-S-methylsulfilimine N-oxide (5) upon analysis by 300 MHz $^1$H NMR and HPLC/MS (mix of isomers). Found: $^1$H NMR (300 MHz, DMSO-d6) δ 8.61 (dd, J=34.8, 1.4 Hz, 1H), 8.03 (dd, J=8.4, 4.2 Hz, 1H), 7.81-7.44 (m, 1H), 4.62 (p, J=7.0 Hz, 1H), 2.75 (d, J=19.9 Hz, 3H), 1.71 (dd, J=7.2, 2.6 Hz, 3H). ESI MS (m/z) 278 [M+H]$^+$. MP=139-141° C. (d).

Example 4

Preparation of N-Cyano-S-[1-(6-trifluoromethyl-3-pyridiny)ethyl]-S-methylsulfoximine N-oxide (6)

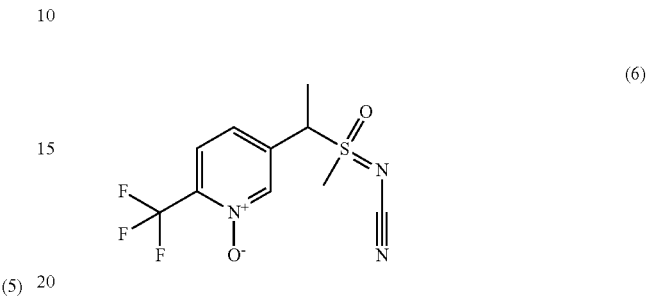

(6)

1.3 g (4.7 moles) N-Cyano-S-[1-(6-trifluoromethyl-3-pyridinyl)ethyl]-S-methylsulfilimine N-oxide (5) and 100 mL of methylene chloride were added to a dry 250 mL round-bottom flask equipped with a magnetic stirrer, nitrogen inlet, addition funnel, thermometer, and reflux condenser. The solution was cooled to 10° C. and 1.7 mL of a 40 wt % sodium permanganate in water solution was added dropwise at a rate that maintained the temperature below 40° C. After this addition was complete, the reaction was stirred at 5° C. for 30 minutes, and allowed to warm to room temperature. HPLC analysis of an aliquot of the reaction mixture indicated that the reaction was essentially complete. The solution was then filtered through filter paper, and the filtrate was washed with sodium bisulfite solution and water. The MDC solution was then dried with anhydrous magnesium sulfate, filtered and concentrated under vacuum on a rotary evaporator. 120 mg of a yellow oil was isolated, and HPLC/MS analysis indicated that it contained a little of the desired product. Based on this analysis, the desired product appears to have poor solubility in MDC. The filter paper from the initial filtration was extracted in about 200 mL of acetone. This extract was then dried over anhydrous magnesium sulfate, filtered and concentrated under vacuum on a rotary evaporator. A sticky yellow solid was isolated and chromatographed on silica gel with a gradient of 25% hexanes/75% acetone transitioning to 100% acetone over 20 minutes. The pure fractions were combined, and stripped to afford 74.1 mg of a white solid which was consistent with the structure assigned to N-Cyano-S-[1-(6-trifluoromethyl-3-pyridinyl)ethyl]-S-methylsulfoximine N-oxide (6) upon analysis by 300 MHz $^1$H NMR and HPLC/MS.

Found: $^1$H NMR (300 MHz, DMSO-d6) δ 8.39 (d, J=1.7 Hz, 1H), 7.85 (d, J=8.5 Hz, 1H), 7.55 (d, J=8.5 Hz, 2H), 4.83 (qd, J=7.1, 2.6 Hz, 1H), 3.25 (d, J=8.0 Hz, 3H), 1.98-1.76 (m, 3H). ESI MS (m/z) 294 [M+H]$^+$. MP=228-231° C.

Examples 5-6

Compounds (9) and (10) of Examples 5 and 6, respectively, are shown in Table 1 below. Compounds (7) and (8) (also shown in Table 1 below) were prepared pursuant to reaction Scheme A illustrated above and utilizing processes similar to those described above in connection with Examples 1 and 2. Compounds (9) and (10) were then prepared from compounds (7) and (8), respectively, utilizing processes similar to those described above in connection with Examples 3 and 4.

TABLE 1

| Starting Compounds | Final Compounds |
|---|---|
| 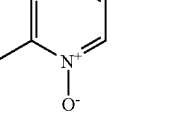 (7) | 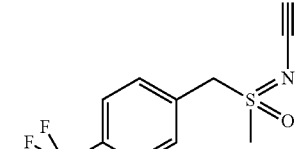 (9) Found: $^1$H NMR (300 MHz, DMSO-d6) δ 8.53 (s, 1H), 8.07 (d, J = 8.4 Hz, 1H), 7.58 (d, J = 8.5 Hz, 1H), 5.18 (s, 2H), 3.51 (s, 3H). ESI MS (m/z) 282 [M + H]+. |
|  (8) | 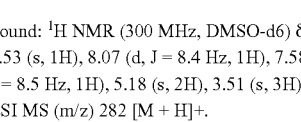 (10) Found: $^1$H NMR (400 MHz, DMSO-d6) δ 8.65 (s, 1H), 8.02 (d, J = 8.6 Hz, 1H), 7.73 (s, 1H), 3.41 (s, 3H), 3.41 (s, 3H), 1.92 (s, 6H). ESI MS (m/z) 308 [M - H]-. |

Example 7

Compound (11) of Example 7 is shown in Table 2 below. Compound (6) was acid hydrolyzed utilizing a process similar to that described herein above to provide compound (11).

TABLE 2

| Starting Compound | Acid Hydrolyzed Compound |
|---|---|
| (6) | (11) Found: $^1$H NMR (300 MHz, DMSO-d6) δ11-10 (bs, 2H) 8.53 (dd, J = 3.9, 1.4 Hz, 1H), 7.97 (dd, J = 8.4, 5.4 Hz, 1H), 7.73-7.48 (m, 1H), 4.99 (dq, J = 14.2, 7.1 Hz, 1H), 3.18 (d, J = 4.6 Hz, 3H), 1.82-1.49 (m, 3H). ESI MS (m/z) 312 [M + H]+. |

While the invention has been illustrated and described in detail in the foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A process for the preparation of a 2-substituted-5-(1-alkylthio)alkyl-pyridine N-oxide according to formula (I),

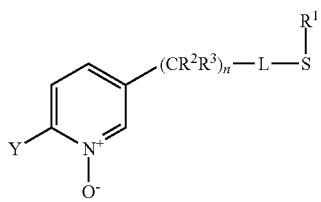
(I)

wherein
L represents a single bond or $R^1$, S and L taken together represent a 4-, 5- or 6-membered ring;
$R^1$ represents $(C_1-C_4)$ alkyl;
$R^2$ and $R^3$ individually represent hydrogen, methyl, ethyl, fluoro, chloro or bromo;
n is an integer from 0-3; and
Y represents $(C_1-C_4)$ haloalkyl;
in which:
i) an enamine according to formula (II)

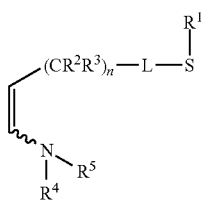
(II)

wherein
$R^1$, $R^2$, $R^3$, L, and n are as previously defined, and $R^4$ and $R^5$ independently represent $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl or heteroaryl or $R^4$ and $R^5$ taken together with N represent a 5- or 6-membered saturated or unsaturated ring is condensed with an α,β-unsaturated ketone according to formula (III)

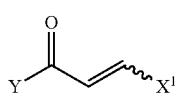
(III)

wherein
Y is as previously defined; and
$X^1$ represents halogen, $OR^6$, $OSO_2R^6$, $SR^6$, $SOR^6$, $SO_2R^6$ or $NR^7R^8$, where $R^6$ represents hydrogen, $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl or heteroaryl; and $R^7$ and $R^8$ independently represent hydrogen, $C_1-C_8$ alkyl, $C_2-C_8$ alkenyl, $C_1-C_8$ arylalkyl, $C_1-C_8$ haloalkyl, $C_1-C_8$ alkoxyalkyl, $C_1-C_8$ alkylaminoalkyl, aryl or heteroaryl or $R^7$ and $R^8$ taken together with N represent a 5- or 6-membered saturated or unsaturated ring;
to provide an intermediate compound according to formula (IV)

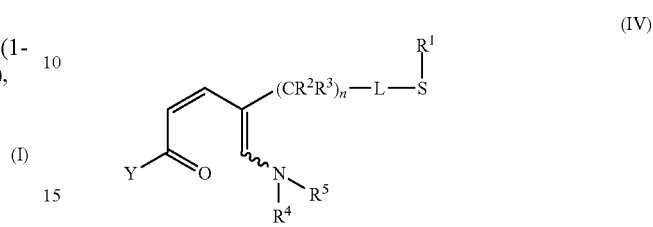
(IV)

wherein
$R^1$, $R^2$, $R^3$, $R^4$, $R^5$, L and n are as previously defined; and
ii) the intermediate compound according to formula (IV) is cyclized using an amine nucleophile according to formula (V)

$$H_2N-X^2$$ (V)

wherein $X^2$ represents hydroxyl.

2. The process of claim 1, wherein cyclization of the intermediate compound according to formula (IV) is performed under refluxing conditions.

3. The process of claim 2, wherein the refluxing conditions include a temperature in the range of 50° C. to 90° C.

4. The process of claim 1, wherein the amine nucleophile is hydroxylamine.

5. The process of claim 4, wherein the hydroxylamine is in the form hydroxylamine hydrochloride.

6. The process of claim 5, wherein the cyclization further includes using a non-nucleophilic base.

7. The process of claim 6, wherein the non-nucleophilic base is triethylamine.

8. The process of claim of claim 1, wherein the enamine according to formula (II) is condensed with the α,β-unsaturated ketone according to formula (III) at a temperature from −20° C. to 35° C.

9. The process of claim 1, wherein the enamine according to formula (II) is condensed with the α,β-unsaturated ketone according to formula (III) at a temperature from −5° C. to 20° C.

10. The process of claim 1, where the enamine according to formula (II) is condensed with the α,β-unsaturated ketone according to formula (III) in a non-polar solvent.

11. The process of claim 10, wherein the non-polar solvent is toluene.

12. The process of claim 1, wherein Y is $CF_3$.

13. The process of claim 1, wherein $R^2$ and $R^3$ independently represent hydrogen, methyl or ethyl.

14. The process of claim 1, wherein $R^2$, $R^3$, n, and Y are as previously defined, $R^1$ represents $CH_3$, L represents a single bond and the compound of formula (I) has the structure

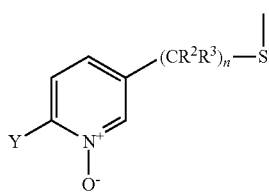

wherein n=1-3.

15. The process of claim 14, wherein Y represents $(C_1\text{-}C_4)$ haloalkyl, $R^2$ and $R^3$ individually represent hydrogen, methyl, ethyl, fluoro, chloro or bromo, and n is an integer from 1-3.

16. The process of claim 15, wherein Y represents $CF_3$, $R^2$ and $R^3$ individually represent hydrogen, methyl or ethyl, and n is an integer from 1-3.

17. The process of claim 1, which further includes the preparation of a compound according to formula (VI)

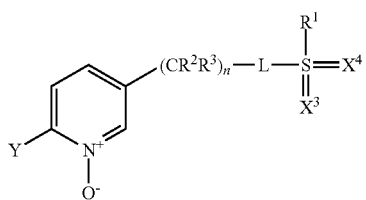

wherein
$R^1$, $R^2$, $R^3$, L, n and Y are as previously defined;
$X^3$ is optional and represents O when present;
$X^4$ represents $NNO_2$, NCN, $NCOOR^9$ or $NCONH_2$; and
$R^9$ represents $(C_1\text{-}C_3)$ alkyl;
in which:
a compound according to formula (I) is reacted with one or more reactants suitable for the addition of $X^4$ and optionally $X^3$.

18. A process for the preparation of a compound according to formula (VI)

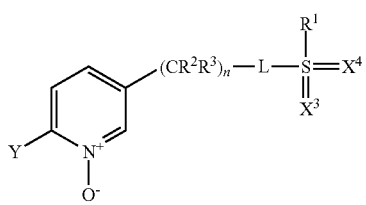

wherein
L represents a single bond or $R^1$, S and L taken together represent a 4-, 5- or 6-membered ring;
$R^1$ represents $(C_1\text{-}C_4)$ alkyl;
$R^2$ and $R^3$ individually represent hydrogen, methyl, ethyl, fluoro, chloro or bromo;
n is an integer from 0-3; and
Y represents $(C_1\text{-}C_4)$ haloalkyl;
$X^3$ is optional and represents O when present;
$X^4$ represents $NNO_2$, NCN, $NCOOR^9$ or $NCONH_2$; and
$R^9$ represents $(C_1\text{-}C_3)$ alkyl;

in which:
a compound according to formula (I)

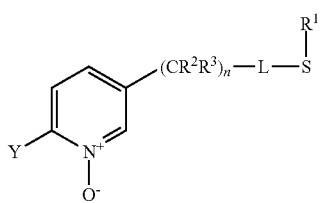

wherein $R^1$, $R^2$, $R^3$, L, n and Y are as previously defined is reacted with one or more reactants suitable for the addition of $X^4$ and optionally $X^3$.

19. A process for the preparation of a 2-substituted-5-(1-alkylthio)alkyl-pyridine N-oxide according to formula (I),

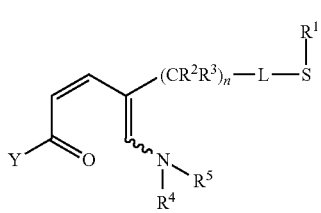

wherein
L represents a single bond or $R^1$, S and L taken together represent a 4-, 5- or 6-membered ring;
$R^1$ represents $(C_1\text{-}C_4)$ alkyl;
$R^2$ and $R^3$ individually represent hydrogen, methyl, ethyl, fluoro, chloro or bromo;
n is an integer from 0-3; and
Y represents $(C_1\text{-}C_4)$ haloalkyl;
in which a compound according to formula (IV)

(IV)

wherein Y, $R^1$, $R^2$, $R^3$, $R^4$, $R^5$, L and n are as previously defined is cyclized using an amine nucleophile according to formula (V)

$$H_2N\text{—}X^2 \qquad (V),$$

wherein $X^2$ represents hydroxyl.

20. The process of claim 19, in which:
an enamine according to formula (II)

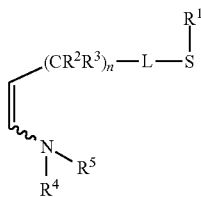
(II)

wherein $R^1$, $R^2$, $R^3$, L, and n are as previously defined, and $R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^4$ and $R^5$ taken together with N represent a 5- or 6-membered saturated or unsaturated ring;

is condensed with an α,β-unsaturated ketone according to formula (III)

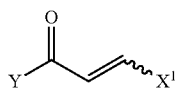
(III)

wherein

Y is as previously defined; and $X^1$ represents halogen, $OR^6$, $OSO_2R^6$, $SR^6$, $SOR^E$, $SO_2R^6$ or $NR^7R^8$, where $R^6$ represents hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl, and $R^7$ and $R^8$ independently represent hydrogen, $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^7$ and $R^8$ taken together with N represent a 5- or 6-membered saturated or unsaturated ring to provide the compound according to formula (IV).

21. The process of claim 19, in which:
an acetyl chloride compound according to formula (VII)

(VII)

wherein Y represents $C_1$-$C_4$ haloalkyl is reacted with an alkyl vinyl ether according to formula (VIII)

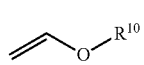
(VIII)

wherein $R^{10}$ represents $C_1$-$C_4$ alkyl to provide an intermediate compound according to formula (IX)

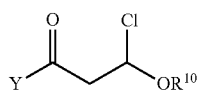
(IX)

and the intermediate compound according to formula (IX) is condensed with an enamine according to formula (II)

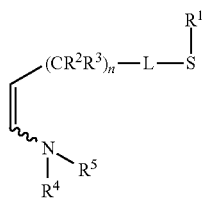
(II)

wherein $R^1$, $R^2$, $R^3$, L, and n are as previously defined, and $R^4$ and $R^5$ independently represent $C_1$-$C_8$ alkyl, $C_2$-$C_8$ alkenyl, $C_1$-$C_8$ arylalkyl, $C_1$-$C_8$ haloalkyl, $C_1$-$C_8$ alkoxyalkyl, $C_1$-$C_8$ alkylaminoalkyl, aryl or heteroaryl or $R^4$ and $R^5$ taken together with N represent a 5- or 6-membered saturated or unsaturated ring to provide the compound according to formula (IV).

\* \* \* \* \*